(12) United States Patent
Fukuda et al.

(10) Patent No.: US 7,724,365 B2
(45) Date of Patent: May 25, 2010

(54) SPECTRAL OBSERVATION METHOD AND SPECTRAL OBSERVATION SYSTEM

(75) Inventors: Yoko Fukuda, Yokohama (JP); Hisashi Okugawa, Yokosuka (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/292,924

(22) Filed: Dec. 1, 2008

(65) Prior Publication Data

US 2009/0116008 A1    May 7, 2009

Related U.S. Application Data

(63) Continuation of application No. PCT/JP2007/000526, filed on May 16, 2007.

(30) Foreign Application Priority Data

Jun. 5, 2006    (JP)    ............................. 2006-156500

(51) Int. Cl.
*G01N 21/64*    (2006.01)
(52) U.S. Cl. ..................... 356/318; 250/458.1
(58) Field of Classification Search ................. 356/317, 356/318
See application file for complete search history.

(56) References Cited

U.S. PATENT DOCUMENTS

| 5,171,534 | A | 12/1992 | Smith et al. |
| 6,414,805 | B1 | 7/2002 | Reichman et al. |
| 6,510,001 | B1 | 1/2003 | Engelhardt et al. |
| 6,858,852 | B2 | 2/2005 | Wolleschensky et al. |
| 2002/0036824 | A1 | 3/2002 | Sasaki |
| 2003/0058440 | A1 | 3/2003 | Scott et al. |
| 2004/0146913 | A1 | 7/2004 | Hirano et al. |

FOREIGN PATENT DOCUMENTS

| JP | A-4-127039 | 4/1992 |
| JP | A-2002-287034 | 10/2002 |
| JP | A-2004-506191 | 2/2004 |
| JP | A-2004-093286 | 3/2004 |
| JP | A-2005-524051 | 8/2005 |
| WO | WO 02/48690 A1 | 6/2002 |
| WO | WO 03/021212 A1 | 3/2003 |

OTHER PUBLICATIONS

European Patent Office, *Supplementary and Annex to the European Search Report on European Patent Application No.* EP 07 73 7182, dated Feb. 16, 2010, pp. 1-8.

*Primary Examiner*—F. L Evans
(74) *Attorney, Agent, or Firm*—Oliff & Berridge, PLC

(57) ABSTRACT

A proposition of the present invention is to acquire necessary data without any chasm in an observation of a specimen containing plural kinds of substances of which exciting wavelengths are different. Accordingly, a spectral observation method of the present invention, irradiating light to the specimen containing plural kinds of substances (RFP, GFP, and so on) of which exciting wavelengths are different, and detecting spectra of light emitted from the specimen, the spectral observation method sequentially acquires spectral data of substances from the one of which exciting wavelength is long while switching a wavelength of the irradiated light among respective exciting wavelengths of the plural kinds of substances, and excludes the exciting wavelength of the substance corresponding to the spectral data to be acquired from detection wavelengths of the spectra each when acquiring the spectral data of the spectral data of the respective substances.

10 Claims, 6 Drawing Sheets

SPECTRAL OBSERVATION METHOD AND SPECTRAL OBSERVATION SYSTEM

CROSS-REFERENCE TO RELATED APPLICATION

This application is a Continuation Application of International Application No. PCT/JP2007/000526, filed May 16, 2007, designating the U.S., in which the International Application claims a priority date of Jun. 5, 2006, based on prior filed Japanese Patent Application No. 2006-156500, the entire contents of which are incorporated herein by reference.

BACKGROUND

1. Field

The present invention relates to a spectral observation method and a spectral observation system of a specimen containing plural kinds of substances of which exciting wavelengths are different, such as a multiple dyeing sample with plural kinds of fluorescent reagents.

2. Description of the Related Art

A spectral imaging fluorescent laser microscope is effective for an observation of a multiple dyeing sample with plural kinds of fluorescent reagents (refer to Japanese Translation of PCT Publication No. 2004-506191, and so on). This laser microscope irradiates excitation light to the sample, performs a spectral diffraction of fluorescence generated there by a grating (diffraction grating) and so on, and detects intensity of each wavelength component after spectral diffraction by a spectral detector. It is also necessary in this laser microscope to cut excessive excitation light reflected by a surface of the sample, a surface of a lens and so on at any place so as not to prevent the observation, as same as the other fluorescent microscopes.

However, it is necessary to secure a wide wavelength band of the fluorescence in this laser microscope performing the spectral detection, and therefore, a specific channel of the spectral detectors corresponding to an exciting wavelength is excluded from a detection wavelength range of the spectral detector (a masking shield is disposed (fixed) in front of the channel) instead of inserting a barrier filter into an optical path of the fluorescence. When the sample is dyed with two kinds of fluorescent reagents, it is conceivable that each of two channels corresponding to these exciting wavelengths are excluded from the detection wavelength range, and then, these fluorescent reagents are excited simultaneously or sequentially to perform a spectral imaging thereof.

However, there is a possibility in which a part of necessary data may be lost in the spectral imaging as stated above. It is because a necessary wavelength may be excluded from (lost) the detection wavelength range when the exciting wavelength of a certain fluorescent reagent is included in a wavelength range of an emission spectrum of the other fluorescent reagent.

SUMMARY

A proposition of the present invention is to provide a spectral observation method and a spectral observation system capable of acquiring necessary data without any chasm, in an observation of a specimen containing plural kinds of substances of which exciting wavelengths are different.

In a spectral observation method of the present invention, irradiating light to a specimen containing plural kinds of substances of which exciting wavelengths are different, and detecting spectra of light emitted from the specimen, the spectral observation method sequentially acquires spectral data of the substances from the one of which exciting wavelength is long while switching a wavelength of the irradiated light among respective exciting wavelengths of the plural kinds of substances, and excludes the exciting wavelength of the substance corresponding to the spectral data to be acquired from detection wavelengths of the spectra each when acquiring the spectral data of the respective substances.

Incidentally, the acquired spectral data may be synthesized.

Besides, a spectral observation system of the present invention includes a spectral observation apparatus including, an irradiating unit irradiating light to a specimen containing plural kinds of substances of which exciting wavelengths are different, a detecting unit detecting spectra of light emitted from the specimen, and a wavelength switching unit switching a wavelength of the light irradiated by the irradiating unit, a controlling device sequentially acquiring spectral data of the substances from the one of which the exciting wavelength is long while switching a wavelength of the irradiated light among respective exciting wavelengths of the plural kinds of substances by controlling the wavelength switching unit, and a movable masking mechanism excluding the exciting wavelength of the substance corresponding to the spectral data to be acquired from detection wavelengths of the spectra each when acquiring the spectral data of the respective substances.

Besides, another spectral observation system of the present invention includes a spectral observation apparatus including, an irradiating unit irradiating light to a specimen containing plural kinds of substances of which exciting wavelengths are different, a detecting unit detecting spectra of light emitted from the specimen, and a wavelength switching unit switching a wavelength of the light irradiated by the irradiating unit, a controlling device sequentially acquiring spectral data of the substances from the one of which exciting wavelength is long while switching a wavelength of the irradiated light among respective exciting wavelengths of the plural kinds of substances by controlling the wavelength switching unit, and a range switching unit switching a detection wavelength range of the detecting unit, and the controlling device excludes a same wavelength as the exciting wavelength of the substance which source of acquired of the data from the detection wavelengths of the spectra by controlling the range switching unit, whenever the spectral data of the respective substances are acquired.

Incidentally, the controlling device may synthesize the acquired spectral data.

According to the present invention, a spectral observation method and a spectral observation system capable of acquiring necessary data without any chasm are realized, in an observation of a specimen containing plural kinds of substances of which exciting wavelengths are different.

DETAILED DESCRIPTION OF THE EMBODIMENTS

First Embodiment

Hereinafter, a first embodiment of the present invention is described. The present embodiment is an embodiment of a spectral imaging fluorescent laser microscope system.

First, a configuration of the present system is described.

Figure 1:
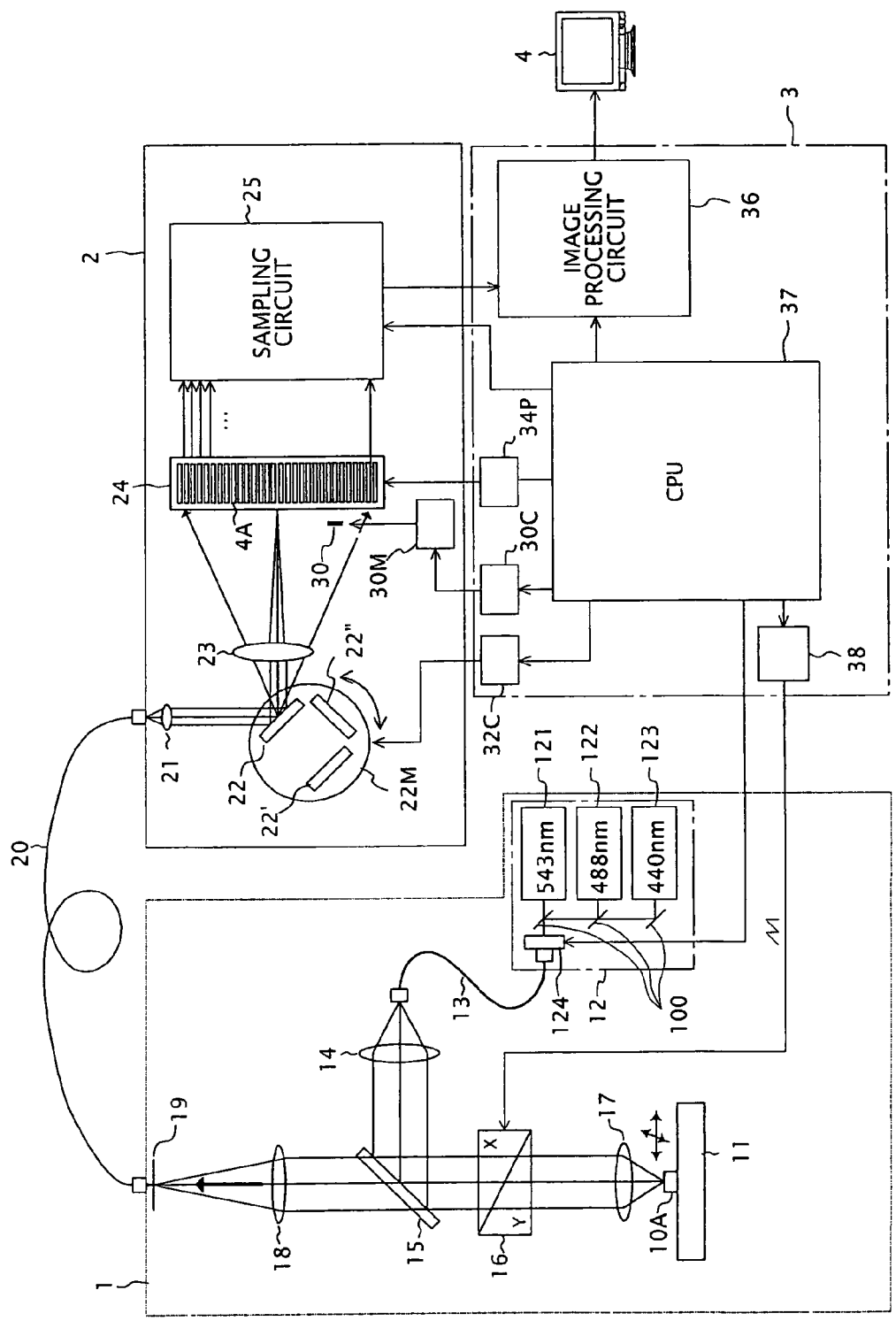
FIG. 1 is a configuration chart of the present system.

FIG. 1 is a configuration chart of the present system. As shown in FIG. 1, a confocal microscope 1, a spectral detecting part 2, a controlling part 3, and a monitor 4 are included in the present system.

The confocal microscope 1 includes a sample stage 11, a laser unit 12, an optical fiber 13, a collimating lens 14, a dichroic mirror 15, an XY scanner 16, an objective lens 17, an image forming lens 18, a pinhole plate 19, and an optical fiber 20. A multiple dyeing sample 10A with plural kinds of fluorescent reagents is supported on the sample stage 11. Details of these fluorescent reagents are described later.

The laser unit 12 includes, for example, plural kinds of laser light sources 121, 122, 123, and a wavelength tunable filter (AOTF, and so on) 124. It is possible to switch wavelengths of emitted laser light (laser wavelength) by an operation of the wavelength tunable filter 124 (or a laser shutter 100). Here, it is assumed that the laser wavelengths are switched among three wavelengths of 543 nm, 488 nm, and 440 nm.

The laser light radiated from the laser unit 12 is collected to one point of the sample 10A via the optical fiber 13, the collimating lens 14, the dichroic mirror 15, the XY scanner 16, and the objective lens 17 sequentially, to excite a specific fluorescent material exciting therein. Fluorescence generated at the fluorescent material is guided to the spectral detecting part 2 via the objective lens 17, the XY scanner 16, the dichroic mirror 15, the image forming lens 18, the pinhole plate 19, and the optical fiber 20 sequentially. Excessive light ray is cut at the pinhole plate 19.

A collimating lens 21, a grating 22, a grating stage 22M, a collecting lens 23, a masking shield 30, a sliding mechanism 30M, a spectral detector 24, and a sampling circuit 25 are included in the spectral detecting part 2.

The grating 22 is supported by the grating stage 22M, and an insertion angle for an optical path is adjustable. The grating stage 22M supports gratings 22',22" of which lattice pitches are different together with the grating 22, and therefore, it is possible to switch the grating inserted into the optical path among the gratings 22, 22', 22".

The spectral detector 24 is formed by arranging plural photomultiplier tubes (PMT) 4A reacting fluorescence with weak intensity, in a linear-array state. Electric power necessary for this spectral detector 24 is supplied from a high-voltage power supply 34P inside the controlling part 3. One PMT 4A constitutes one channel of the spectral detector 24. Hereinafter, the number of arrays of the PMTs 4A (namely, the number of channels of the spectral detector 24) is set to be 32.

The masking shield 30 is a mask in a strip state to shield any one of channels of the spectral detector 24, and is supported by the sliding mechanism 30M. The sliding mechanism 30M slides the masking shield 30 in an array direction of the channels, and thereby, the channel which is to be masked can be switched. Besides, the sliding mechanism 30M disposes the masking shield 30 at a vacating position, and thereby, all of the 32 channels can be opened.

The fluorescence guided to the spectral detecting part 2 is incident on the grating 22 via the collimating lens 21, and then, a spectral decomposition is performed for the fluorescence into respective wavelength components. The respective wavelength components are individually incident on the 32 channels of the spectral detector 24, and respectively converted into electrical signals in accordance with the intensity thereof. Incidentally, the light is not incident on the channel where the masking shield 30 is disposed, and therefore, an electrical signal corresponding to the intensity of "0" (zero) is generated at the channel. The 32 electrical signals generated at the 32 channels are sampled at a certain timing by the sampling circuit 25, and sequentially transmitted to the controlling part 3. The 32 electrical signals transmitted at this time are spectral data at one point of the sample 10A (a laser light collection point).

An image processing circuit 36, a CPU 37, an XY scanner driving circuit 38, a grating driving circuit 32C, a masking shield driving circuit 30C, and the high-voltage power supply 34P are included in the controlling part 3. Hereinafter, it is described on an assumption in which a ROM storing operation programs of the CPU 37 and a RAM used as a primary storage during operation of the CPU 37 are mounted on the CPU 37, and a memory capable of storing spectral image data (it will be described later) for plural frames is mounted on the image processing circuit 36.

The CPU 37 two-dimensionally scans the sample 10A at the laser light collection point by driving the XY scanner 16 of the confocal microscope 1 via the XY scanner driving circuit 38. Besides, the CPU 37 repeatedly gives instructions of sampling for the sampling circuit 25 during this scanning, and sequentially downloads the spectral data at respective points of the sample 10A to the image processing circuit 36. According to this operation of the CPU 37, the spectral image data for one frame of the sample 10A are stored into the memory inside the image processing circuit 36 before the two-dimensional scanning of the sample 10A is finished (individual pixel has values for 32 channels as the spectral data). Hereinafter, the operation of the CPU 37 to acquire the spectral image data as stated above is called as "spectral imaging". The image processing circuit 36 generates image data for a monitor display if necessary based on the spectral image data acquired by this spectral imaging, and transmits it to the monitor 4.

Incidentally, continuous acquisition of the spectral image data (real time imaging) is also possible if the CPU 37 repeats the spectral imaging.

Besides, it is possible for the CPU 37 to perform an on/off control of the laser light and a wavelength switching control of the laser light by giving an instruction to the wavelength tunable filter 124 (or each laser shutter 100) inside the laser unit 12 at the time of the spectral imaging.

Further, it is possible for the CPU 37 to change the detection wavelength range of the spectral detector 24 by driving the grating stage 22M via the grating driving circuit 32C, or by driving the sliding mechanism 30M via the masking shield driving circuit 30C, at the time of the spectral imaging.

Incidentally, the grating to be inserted into the optical path may be switched among the gratings 22, 22', 22" to increase or decrease the detection wavelength range of the spectral detector 24. However, when the detection wavelength range is increased or decreased, wavelength resolving power may change accordingly, because the number of channels of the spectral detector 24 is constant. For example, the detection wavelength range is 80 nm and the wavelength resolving power is 2.5 nm when the grating 22 is inserted into the optical path, the detection wavelength range is 160 nm and the wavelength resolving power is 5 nm when the grating 22' is inserted into the optical path, the detection wavelength range is 320 nm and the wavelength resolving power is 10 nm when the grating 22" is inserted into the optical path.

Besides, the insertion angle of the inserted grating may be changed to change an upper limit of the detection wavelength range of the spectral detector 24 toward a short-wavelength side or to change a lower limit of the detection wavelength range toward a long-wavelength side.

Further, the masking shield 30 may be disposed at the channel corresponding to a specific wavelength component among the 32 channels of the spectral detector 24 to exclude the specific wavelength component from the detection wavelength range of the spectral detector 24.

Next, the sample 10A of the present system is described.

Figure 2:
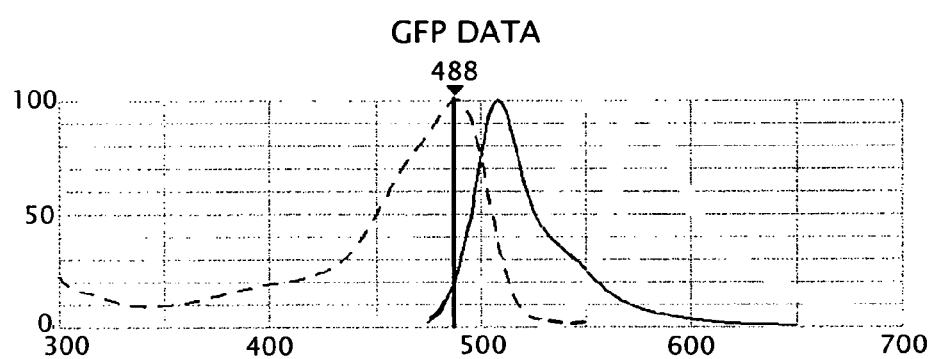
FIG. 2 is a view showing characteristics unique to GFP.
Figure 3:
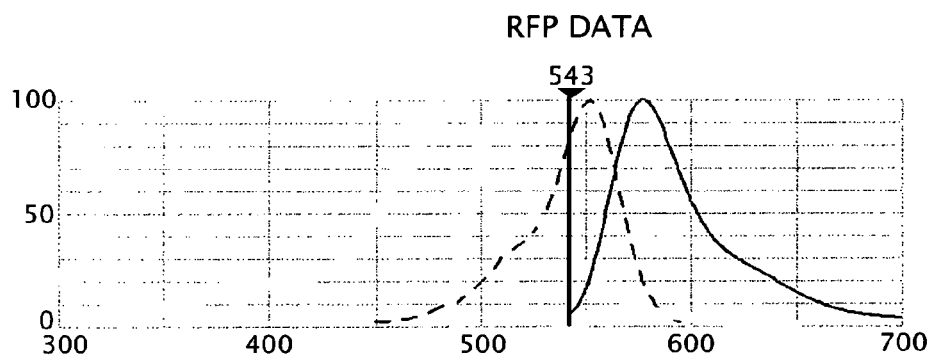
FIG. 3 is a view showing characteristics unique to RFP.

The sample 10A is a sample of a multiple dyeing living cell with two kinds of fluorescent reagents of GFP, RFP. FIG. 2 is a view showing characteristics unique to the GFP, and FIG. 3 is a view showing characteristics unique to the RFP. In each of FIG. 2 and FIG. 3, a dotted line shows an absorption spectrum, a solid line shows an emission spectrum, and a heavy linear line shows an exciting wavelength.

First, the exciting wavelength of the GFP is 488 nm, and a wavelength range of the emission spectrum of the GFP is approximately 450 nm to approximately 650 nm, as shown in FIG. 2. A channel at 488 nm is excluded from the detection wavelength range, and the spectral imaging is performed while exciting with the laser light of 488 nm, to know a contribution of the GFP as stated above in the sample 10A by the present system. Data showing the contribution of the GFP (GFP data) is reflected on the data mainly at the long-wavelength side than 488 nm among the acquired spectral image data.

On the other hand, the exciting wavelength of the RFP is 543 nm which is longer than that of the GFP, and a wavelength rage of the emission spectrum of the RFP is approximately 550 nm to approximately 700 nm as shown in FIG. 3. A channel at 543 nm is excluded from the detection wavelength range, and the spectral imaging is performed while exciting with the laser light of 543 nm to know a contribution of the RFP as stated above in the sample 10A by the present system. Data showing the contribution of the RFP (RFP data) is reflected on the data mainly at the long-wavelength side than 543 nm among the acquired spectral image data.

However, when the spectral imaging is performed while performing a simultaneous excitation of the GFP and the RFP, a relatively important portion of the GFP data (a portion in a vicinity of 543 nm) are lost because it is necessary to exclude both the channel at 488 nm and the channel at 543 nm from the detection wavelength range.

Besides, when the spectral imaging of the GFP of which exciting wavelength is short (namely, it requires high energy for the excitation) is performed before the spectral imaging of the RFP of which exciting wavelength is long (namely, it does not require high energy for the excitation) is performed, the RFP data cannot be acquired accurately because the RFP reacts before the RFP data is acquired and fading thereof begins, even if the spectral imaging is performed by exciting the GFP and the RFP separately. This is obvious from the fact that the exciting wavelength of the GFP (the heavy linear line in FIG. 2) is included in the wavelength range of the absorption spectrum of the RFP (the dotted line in FIG. 3).

Incidentally, it is assumed that the respective exciting wavelengths of the fluorescent reagents added to the sample 10A are recognized by the CPU 37 of the present system.

Information of these exciting wavelengths is input to the present system in advance from external via a not-shown interface provided at the controlling part 3.

Next, an operation procedure of the CPU 37 is described. The CPU 37 operates in accordance with the following procedure to avoid the above-stated problems.

Figure 4:
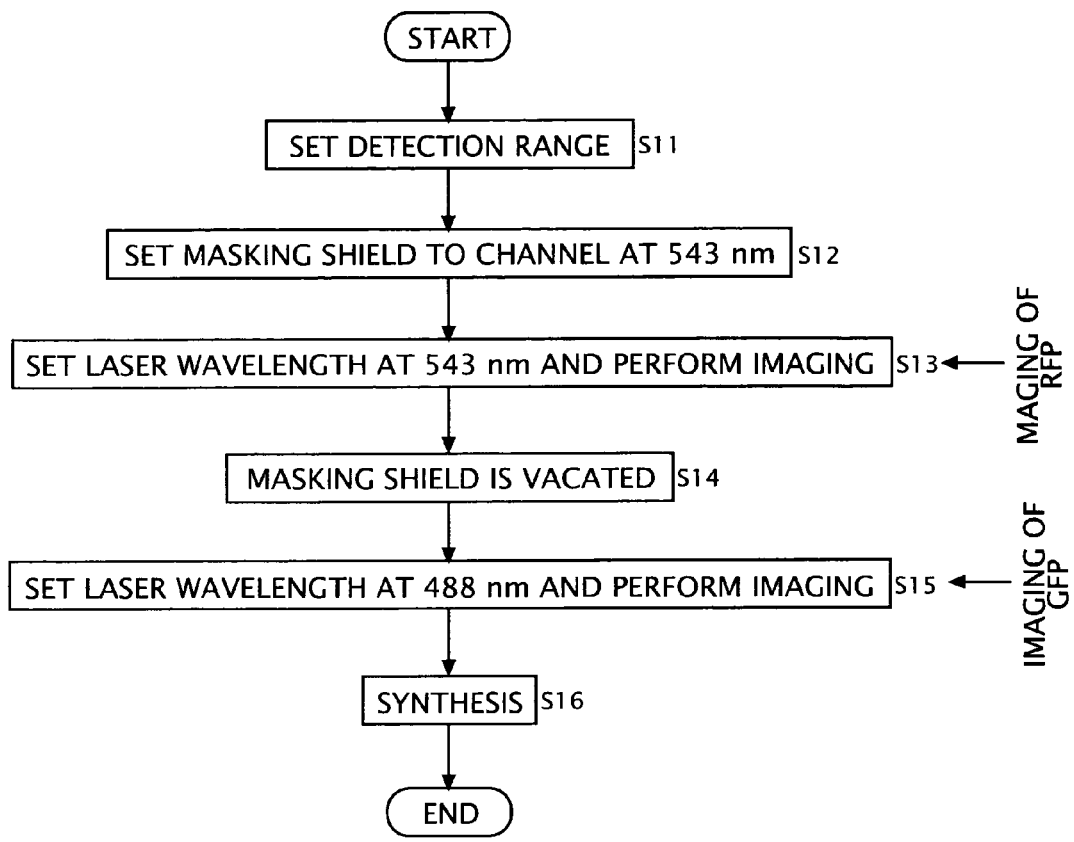
FIG. 4 is an operation flowchart of a CPU 37 of a first embodiment.
Figure 5:
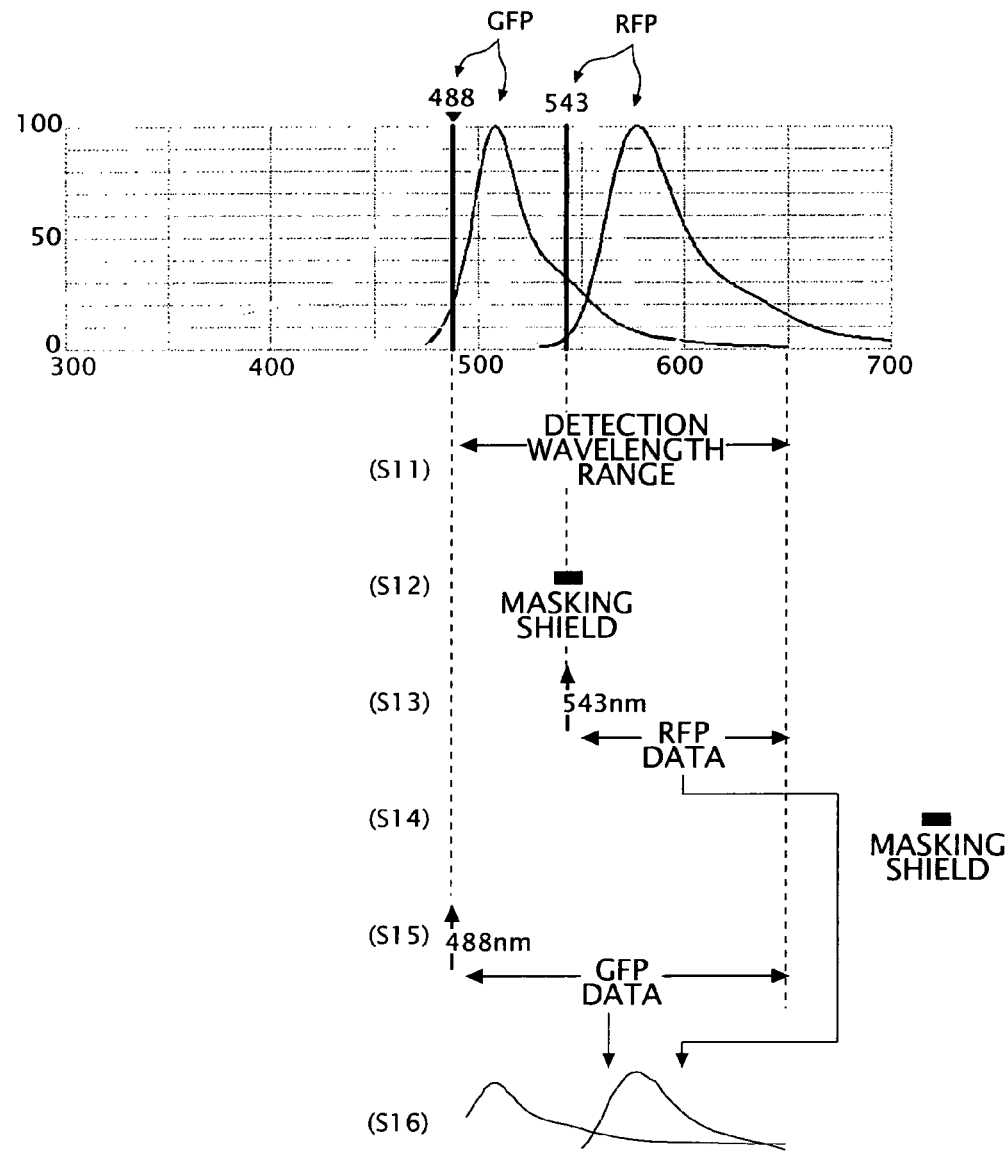
FIG. 5 is a view in which contents of respective steps in FIG. 4 are visualized.

FIG. 4 is an operation flowchart of the CPU 37. When contents of the respective steps in FIG. 4 are visualized, they become as shown in FIG. 5. First, the CPU 37 sets the detection wavelength range of the spectral detector 24 from 490 nm to 650 nm, and the wavelength resolving power at 5 nm (step S11), as shown in these FIG. 4 and FIG. 5. This detection wavelength range (490 nm to 650 nm) covers the main wavelength range of the emission spectrum of the GFP and the main wavelength range of the emission spectrum of the RFP, and it is out of the exciting wavelength of the GFP (488 nm).

Next, the CPU 37 sets a subject to be masked of the masking shield 30 to the channel at 543 nm, to exclude the channel from the detection wavelength range (step S12). This wavelength is the exciting wavelength of the RFP.

The CPU 37 sets the laser wavelength at 543 nm in the state as stated above, and performs the spectral imaging (step S13). The CPU 37 regards all data at the long-wavelength side than 543 nm (from 551 nm to the upper limit) among the acquired spectral image data as available data. Incidentally, the excitation light at 543 nm excites the RFP, but does not excite the GFP of which exciting wavelength is shorter than 543 nm, and therefore, it is conceivable that only the RFP data is reflected on this available data.

Subsequently, the CPU 37 disposes the masking shield 30 at the vacating position (step S14). Accordingly, all of the channels from 490 nm to 650 nm become the detection wavelength range.

The CPU 37 sets the laser wavelength at 488 nm in the state as stated above, and performs the spectral imaging (step S15). The CPU 37 regards all data at the long-wavelength side than 488 nm (from 496 nm to the upper limit) among the acquired spectral image data as the available data. Incidentally, the excitation light of 488 nm excites the GFP, and therefore, the GFP data is reflected on this available data. Besides, the excitation light at 488 nm excites the RFP a little bit, and therefore, the wavelength range of the emission spectrum of the RFP is also included in the wavelength range of the available data. Accordingly, it is conceivable that the RFP data is also reflected on this available data a little bit.

After that, the CPU 37 reads out the available data acquired at the step S13 (the spectral image data from 551 nm to the upper limit) and the available data acquired at the step S15 (the spectral image data from 496 nm to the upper limit) from the memory inside the image processing circuit 36, and synthesizes these data (step S16). This synthesis is an addition (integration) synthesis, and values of the same pixels of the same channels are added (integrated) with each other among these available data. The spectral image data acquired after the addition (integration) (synthesized spectral image data) can be regarded to be equal to the spectral image data acquired when the GFP and the RFP are simultaneously excited. Accordingly, the CPU 37 gives an instruction to the image processing circuit 36 to perform a well-known unmixing calculation for the synthesized spectral image data. The GFP data and the RFP data included in the synthesized spectral image data are completely separated by this unmixing, and each of the contribution of the GFP and the contribution of the RFP become accurately known. These acquired information is output to the monitor 4 if necessary.

Incidentally, information required for the unmixing (information of the emission spectrum of the GFP and the emission spectrum of the RFP) is input to the present system in advance from external via the not-shown interface provided at the controlling part 3 together with the above-stated information of the exciting wavelength.

As stated above, the CPU 37 of the present system performs the spectral imaging for two times while switching the wavelength of the laser light between each of the exciting wavelengths of the two fluorescent reagents (RFP, GFP), and sequentially acquires the spectral data mainly relating to the RFP (the available data at the step S13) and the spectral data mainly relating to the GFP (the available data at the step S15).

Consequently, it is possible to acquire each of the main part of the RFP data and the main part of the GFP data without any chasm even though the channels corresponding to the exciting wavelengths are excluded from the detection wavelength range in each spectral imaging.

Besides, the CPU 37 of the present system performs the spectral imaging of which exciting wavelength is long (the spectral imaging relating to the RFP) first, and therefore, it is avoided that the spectral imaging relating to one fluorescent reagent interferes the other fluorescent reagent (causes the fading). Accordingly, each of the spectral data of the two fluorescent reagents can be acquired accurately.

Further, the CPU 37 of the present system synthesizes both of the available data after the wavelength range of the available data acquired at the step S15 is overlapped on the wavelength range of the available data acquired at the step S13. And, the image processing circuit 36 of the present system performs the unmixing calculation for the synthesized spectral data. Accordingly, it is possible to acquire the spectral data of the two fluorescent reagents more accurately.

Incidentally, the CPU 37 of the present embodiment overlaps the wavelength range of the available data acquired at the step S15 on the wavelength range of the available data acquired at the step S13, but both of the wavelength ranges may be separated. In this case, the synthesis procedure (step S16) may not be performed. For example, the CPU 37 creates an image showing a spatial distribution of the RFP in a sample 10A based on the available data acquired at the step S13, and creates an image showing a spatial distribution of the GFP in the sample 10A based on the available data acquired at the step S15, and may display them on the monitor 4.

Second Embodiment

Hereinafter, a second embodiment of the present invention is described. The present embodiment is also an embodiment of a spectral imaging fluorescent laser microscope system. Here, only different points from the first embodiment are described. The different points exist in fluorescent reagents added to the sample 10A and operations of the CPU 37.

First, the fluorescent reagents added to the sample 10A of the present embodiment are described.

The fluorescent reagents added to the sample 10A are three kinds of GFP, RFP, and CFP, and the characteristics unique to the GFP, RFP are the same as they are described in the first embodiment.

Figure 6:
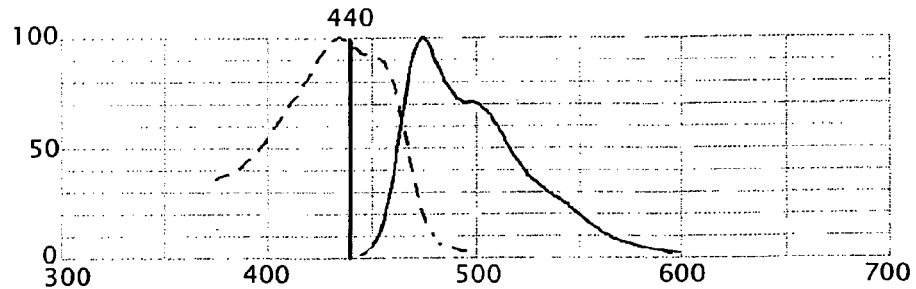
FIG. 6 is a view showing characteristics unique to CFP.

FIG. 6 is a view showing characteristics unique to the CFP. In FIG. 6, a dotted line shows an absorption spectrum, a solid line shows an emission spectrum, and a heavy linear line shows an exciting wavelength. As shown in FIG. 6, an exiting wavelength of the CFP is 440 nm which is shorter than those of the GFP and the RFP, and a wavelength range of the emission spectrum of the CFP is from approximately 450 nm to approximately 600 nm. The channel at 440 nm is excluded from the detection wavelength range, and the spectral imaging is performed while exciting with the laser light at 440 nm to know a contribution of the CFP as stated above in the sample 10A by the present system. Data showing the contribution of the CFP (CFP data) appear in the data mainly at the long-wavelength side than 440 nm among the acquired spectral image data.

Next, an operation procedure of the CPU 37 is described.

Figure 7:
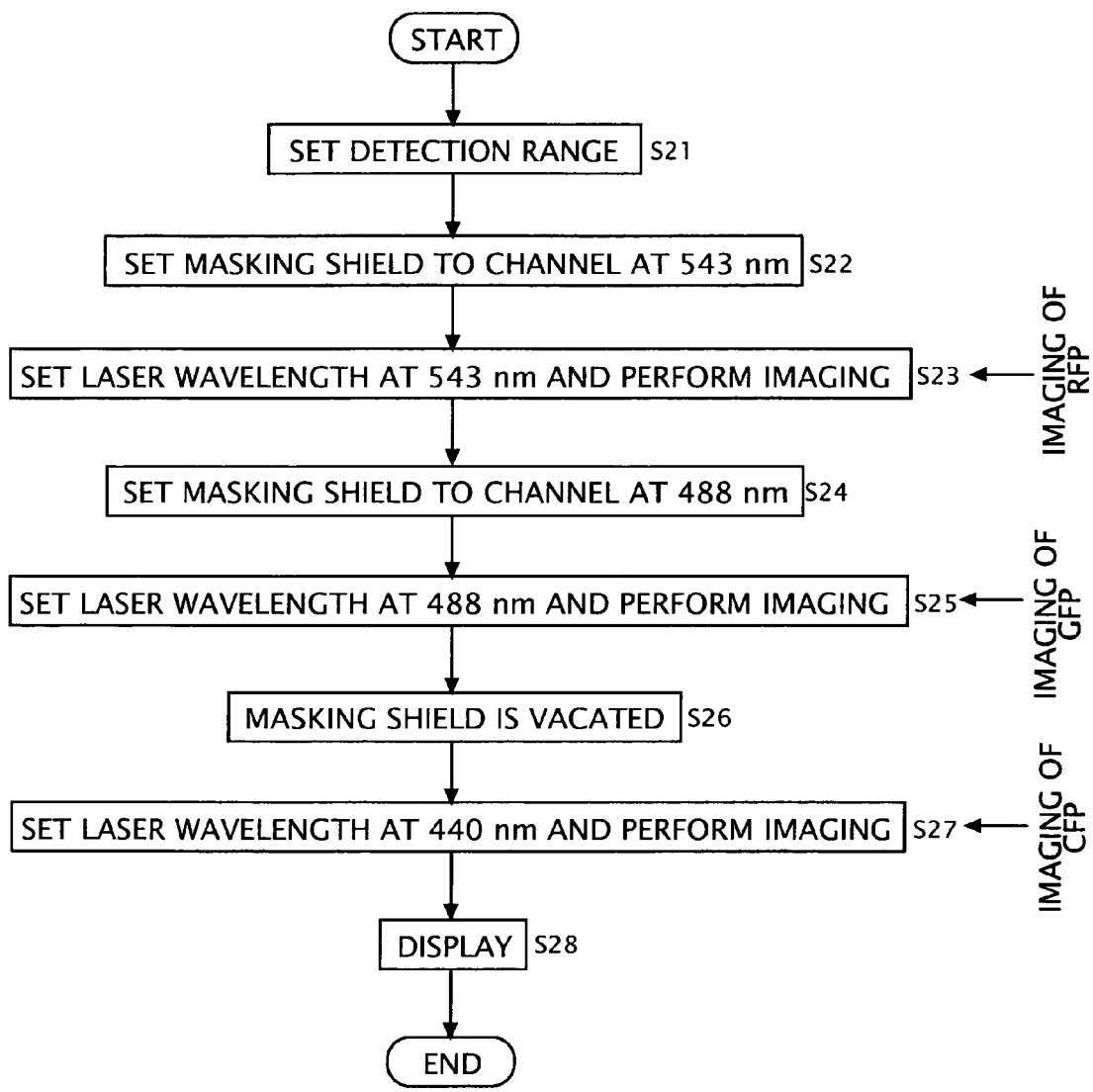
FIG. 7 is an operation flowchart of a CPU 37 of a second embodiment.
Figure 8:
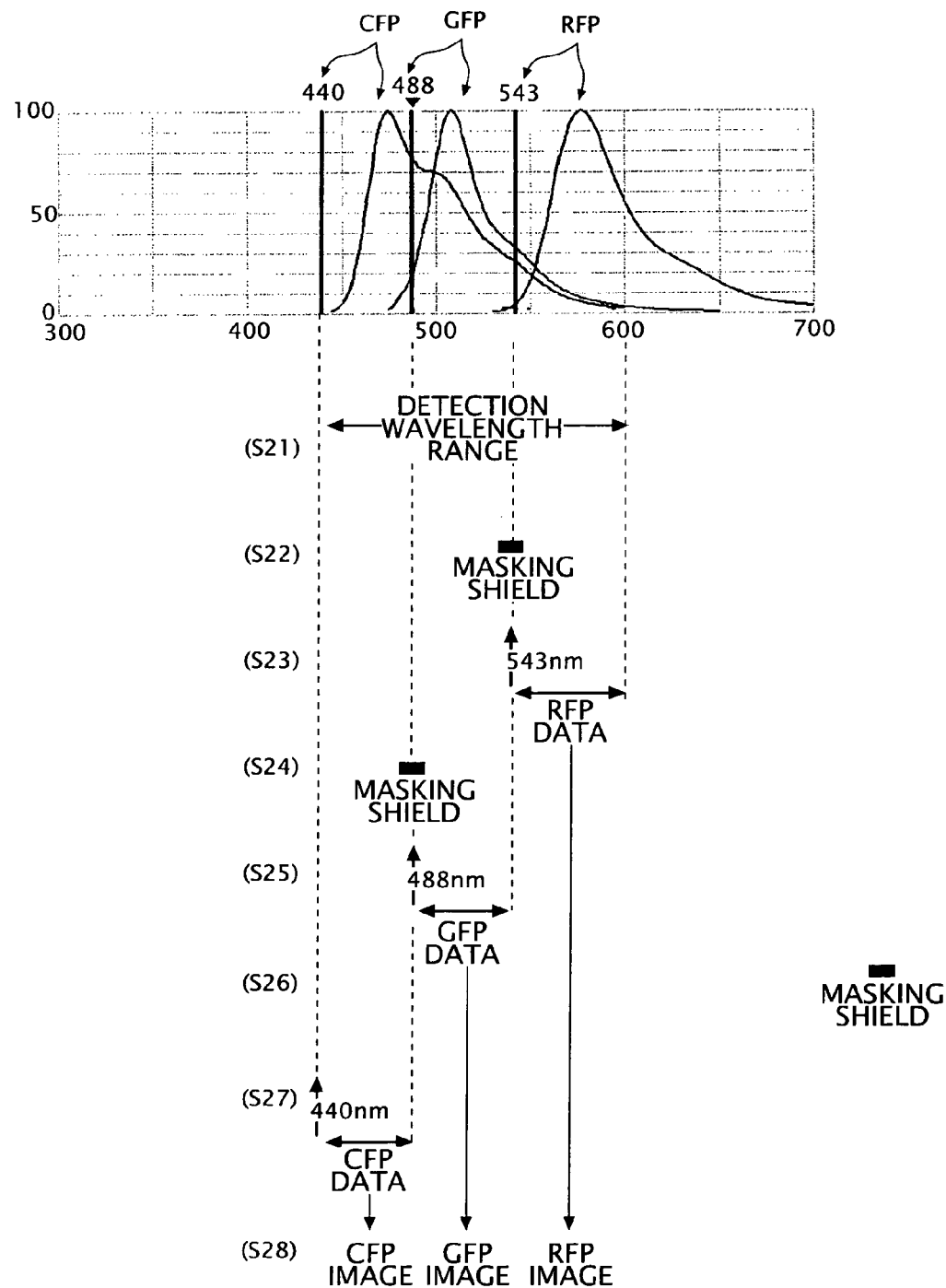
FIG. 8 is a view in which contents of respective steps in FIG. 7 are visualized.

FIG. 7 is an operation flowchart of the CPU 37 of the present embodiment. When contents of the respective steps in FIG. 7 are visualized, they become as shown in FIG. 8. First, the CPU 37 sets the detection wavelength range of the spectral detector 24 from 440 nm to 600 nm, and the wavelength resolving power at 10 nm (step S21), as shown in these FIG. 7 and FIG. 8. This detection wavelength range (440 nm to 600 nm) covers the main wavelength range of the emission spectrum of the CFP, the main wavelength range of the emission spectrum of the GFP, and the main wavelength range of the emission spectrum of the RFP, and this detection wavelength range (440 nm to 600 nm) is out of the exciting wavelength of the CFP (440 nm).

Next, the CPU 37 sets a subject to be masked of the masking shield 30 to the channel at 543 nm, to exclude the channel from the detection wavelength range (step S22). This wavelength is the exciting wavelength of the RFP.

The CPU 37 sets the laser wavelength at 543 nm in the state as stated above, and performs the spectral imaging (step S23). The CPU 37 regards all data at the long-wavelength side than 543 nm (from 558 nm to the upper limit) among the acquired spectral image data as available data. Incidentally, the excitation light at 543 nm excites the RFP, but does not excite the GFP, CFP of which exciting wavelengths are shorter than 543 nm, and therefore, it is conceivable that only the RFP data is reflected on this available data.

Next, the CPU 37 sets a subject to be masked of the masking shield 30 to the channel at 488 nm, to exclude the channel from the detection wavelength range (step S24).

The CPU 37 sets the laser wavelength at 488 nm in the state as stated above, and performs the spectral imaging (step S25). The CPU 37 regards data at the long-wavelength side than 488 nm and at the short-wavelength side than 543 nm (from 503 nm to 528 nm) from among the acquired spectral image data as available data. Incidentally, the excitation light at 488 nm excites the GFP, and therefore, the GFP data is reflected on this available data. Besides, the excitation light at 488 nm excites the RFP only a little bit, but the wavelength range of the emission spectrum of the RFP is seldom included in the wavelength range of this available data. Accordingly, it is conceivable that only the GFP data is reflected on this available data.

Subsequently, the CPU 37 disposes the masking shield 30 at the vacating position (step S26).

The CPU 37 sets the laser wavelength at 440 nm in the state as stated above, and performs the spectral imaging (step S27). The CPU 37 regards data at the long-wavelength side than 440 nm and at the short-wavelength side than 488 nm (from 455 nm to 473 nm) among the acquired spectral image data as available data (refer to FIG. 8). Incidentally, the excitation light at 440 nm excites the CFP, and therefore, the CFP data is reflected on this available data. Besides, the excitation light at 440 nm excites the GFP only a little bit, but the wavelength range of the emission spectrum of the GFP is seldom included in the wavelength range of this available data. Accordingly, it is conceivable that only the CFP data is reflected on this available data.

After that, the CPU 37 reads out the available data acquired at the step S23 (the spectral image data from 558 nm to the upper limit) from the memory inside the image processing circuit 36, creates an image showing a spatial distribution of the RFP in the sample 10A based on the acquired available data, and displays it on the monitor 4. Similarly, the CPU 37 reads out the available data acquired at the step S25 (the spectral image data from 503 nm to 528 nm) from the memory inside the image processing circuit 36, creates an image showing a spatial distribution of the GFP in the sample 10A based on the acquired available data, and displays it on the monitor 4. Further, similarly, the CPU 37 reads out the available data acquired at the step S27 (the spectral image data from 455 nm to 473 nm) from the memory inside the image processing circuit 36, creates an image showing a spatial distribution of the CFP in the sample 10A based on the acquired available data, and displays it on the monitor 4 (step S28).

As stated above, the CPU 37 of the present system performs the spectral imaging for three times while switching the wavelength of the laser light between each of the exciting wavelengths of the three fluorescent reagents (RFP, GFP, CFP), and sequentially acquires the spectral data relating to the RFP (the available data at the step S23) the spectral data relating to the GFP (the available data at the step S25), and the spectral data mainly relating to the CFP (the available data at the step S27).

Consequently, it is possible to acquire each of the main part of the RFP data, the main part of the GFP data, and the main part of the CFP data without any chasm even though the channels corresponding to the exciting wavelengths are excluded from the detection wavelength range in each spectral imaging.

Besides, the CPU 37 of the present system performs the spectral imaging of which exciting wavelength is long first, and therefore, it is avoided that the spectral imaging relating to one fluorescent reagent interferes the other fluorescent reagents (causes the fading). Accordingly, each of the spectral data of the three fluorescent reagents can be accurately acquired.

Incidentally, the CPU 37 of the present embodiment separates a wavelength range (A) of the available data acquired at the step S23, a wavelength range (B) of the available data acquired at the step S25, and a wavelength range (C) of the available data acquired at the step S28, but (B) may be overlapped on (A) by increasing toward the long-wavelength side, and (C) may be overlapped on (B) and (A) by increasing toward the long-wavelength side. In this case, the three available data may be synthesized and then performed the unmixing calculation.

[Other]

Incidentally, a fluorescent microscope system is described in the above-stated respective embodiments, but the present invention is also effective when spectral data of phosphorescence generated at a sample is acquired in addition when the spectral data of the fluorescence generated at the sample is acquired.

Besides, in the above-stated respective embodiments, a microscope system including an imaging function is described, but the present invention is also effective when spectral data of a representative point (plural or a single point(s)) of a sample is acquired.

Further, in the above-stated respective embodiments, a part or all of the processes by the CPU 37 may be executed by dedicated circuits other than the CPU. Besides, a part or all of the processes by the CPU 37 may be executed by a computer connected to the controlling part 3. In this case, processing programs to be executed by the computer may be installed on the computer in advance.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claims is:

1. A spectral observation method, for utilizing a spectral observation system having an irradiating unit that irradiates light to excite a specimen containing plural kinds of substances of which exciting wavelengths are different, and detects spectra of light emitted from the specimen, said spectral observation method comprising:

switching a wavelength of the irradiating light from the irradiating unit in decreasing order of respective exciting wavelengths of the plural kinds of substances;

acquiring spectral data of the substance by detection of light emitted from the specimen at each exciting wavelength; and excluding the exciting wavelength of the substance corresponding to the spectral data to be acquired from detection wavelengths of said spectra each when acquiring the spectral data of said respective substances.

2. The spectral observation method according to claim 1, wherein said acquired spectral data are synthesized.

3. The spectral observation method according to claim 1, wherein the plural kinds of substances include a first substance having a relatively long exciting wavelength and a second substance having a relatively short exciting wavelength, in which the exciting wavelength of the second substance is included in a wavelength range of an absorption spectrum of the first substance, and the exciting wavelength of the first substance is not included in a wavelength range of an absorption spectrum of the second substance.

4. The spectral observation method according to claim 1, wherein said irradiating unit is a laser.

5. A spectral observation system, comprising:

a spectral observation apparatus including, an irradiating unit irradiating light to a specimen containing plural kinds of substances of which exciting wavelengths are different, a detecting unit detecting spectra of light emitted from said specimen, and a wavelength switching unit switching a wavelength of the light irradiated by said irradiating unit;

a controlling device that controls said wavelength switching unit to switch the wavelength of said irradiating light from said irradiating unit in decreasing order of respective exciting wavelength of said plural kinds of substances, controls said irradiating unit to irradiate light at each exciting wavelength, controls said detecting unit to detect spectra of light emitted from the specimen at each exciting wavelength, and controls the acquisition of spectral data of the substance at each exciting wavelength; and a movable masking mechanism excluding the exciting wavelength of the substance corresponding to the spectral data to be acquired from detection wavelengths of said spectra each when acquiring the spectral data of said respective substances.

6. The spectral observation system according to claim 5, wherein said controlling device synthesizes said acquired spectral data.

7. The spectral observation system according to claim 5, wherein
the plural kinds of substances include a first substance having a relatively long exciting wavelength and a second substance having a relatively short exciting wavelength, in which
the exciting wavelength of the second substance is included in a wavelength range of an absorption spectrum of the first substance, and the exciting wavelength of the first substance is not included in a wavelength range of an absorption spectrum of the second substance.

8. A spectral observation system, comprising:
a spectral observation apparatus including,
an irradiating unit irradiating light to a specimen containing plural kinds of substances of which exciting wavelengths are different,
a detecting unit detecting spectra of light emitted from said specimen, and
a wavelength switching unit switching a wavelength of the light irradiated by said irradiating unit;
a controlling device that controls said wavelength switching unit to switch the wavelength of said irradiating light from said irradiating unit in decreasing order of respective exciting wavelength of said plural kinds of substances, controls said irradiating unit to irradiate light at each exciting wavelength, controls said detecting unit to detect spectra of light emitted from the specimen at each exciting wavelength, and controls the acquisition of spectral data of the substance at each exciting wavelength; and
a range switching unit switching a detection wavelength range of said detecting unit, and
wherein said controlling device excludes the exciting wavelength of the substance corresponding to the spectral data to be acquired from the detection wavelengths of said spectra by controlling said range switching unit, each when acquiring the spectral data of said respective substances.

9. The spectral observation system according to claim 8, wherein said controlling device synthesizes said acquired spectral data.

10. The spectral observation system according to claim 8, wherein
the plural kinds of substances include a first substance having a relatively long exciting wavelength and a second substance having a relatively short exciting wavelength, in which
the exciting wavelength of the second substance is included in a wavelength range of an absorption spectrum of the first substance, and the exciting wavelength of the first substance is not included in a wavelength range of an absorption spectrum of the second substance.

* * * * *